United States Patent [19]

Garito et al.

[11] Patent Number: 4,657,016
[45] Date of Patent: Apr. 14, 1987

[54] ELECTROSURGICAL HANDPIECE FOR BLADES, NEEDLES AND FORCEPS

[76] Inventors: Jon C. Garito, 264 Hedge La., Hewlett Harbor, N.Y. 11577; Alan G. Ellman, 1 Auerbach La., Lawrence, N.Y. 11516

[21] Appl. No.: 723,690

[22] Filed: Apr. 16, 1985

Related U.S. Application Data

[63] Continuation-in-part of Ser. No. 642,521, Aug. 20, 1984.

[51] Int. Cl.⁴ .............................................. A61B 17/36
[52] U.S. Cl. ............................ 128/303.13; 339/268 R; 339/270 R
[58] Field of Search ........... 128/303.1, 303.11, 303.12, 128/303.13, 303.14, 303.15, 303.16, 303.17, 303.18, 303.19; 339/268 R, 270 R, 273 R; 219/227, 229, 230, 233, 238

[56] References Cited

U.S. PATENT DOCUMENTS 3,401,371 4/1966 Hammond ...................... 339/268 R
3,742,187 6/1973 Folus ................................ 128/303.1
3,870,047 3/1975 Gonser ........................... 128/303.17

Primary Examiner—Kyle L. Howell
Assistant Examiner—Randy Citrin
Attorney, Agent, or Firm—Rosen, Dainow & Jacobs

[57] ABSTRACT

A handpiece adapted for use with a plurality of different electrosurgical electrodes. The handpiece comprises a collet in which a central bore for receiving adaptors and electrodes extends axially from an endface, slits for receiving the flat end of a scalpel blade extend radially from the central bore, and a pair of axial bores for receiving the two pins of electrocoaptation forceps are diametrically arranged with respect to the central bore. The bore of an insulating sleeve and the outer surface of the collet cooperate to compress the slitted portion of the collet during relative rotation in a first direction. A forceps adaptor is provided for coupling forceps to a handpiece without diametrically opposed bores. The pin of the adaptor is inserted in the central bore of the collet and a pair of flexible tubes, electrically connected to the adaptor pin, are adapted to receive the pins formed on forceps.

13 Claims, 20 Drawing Figures

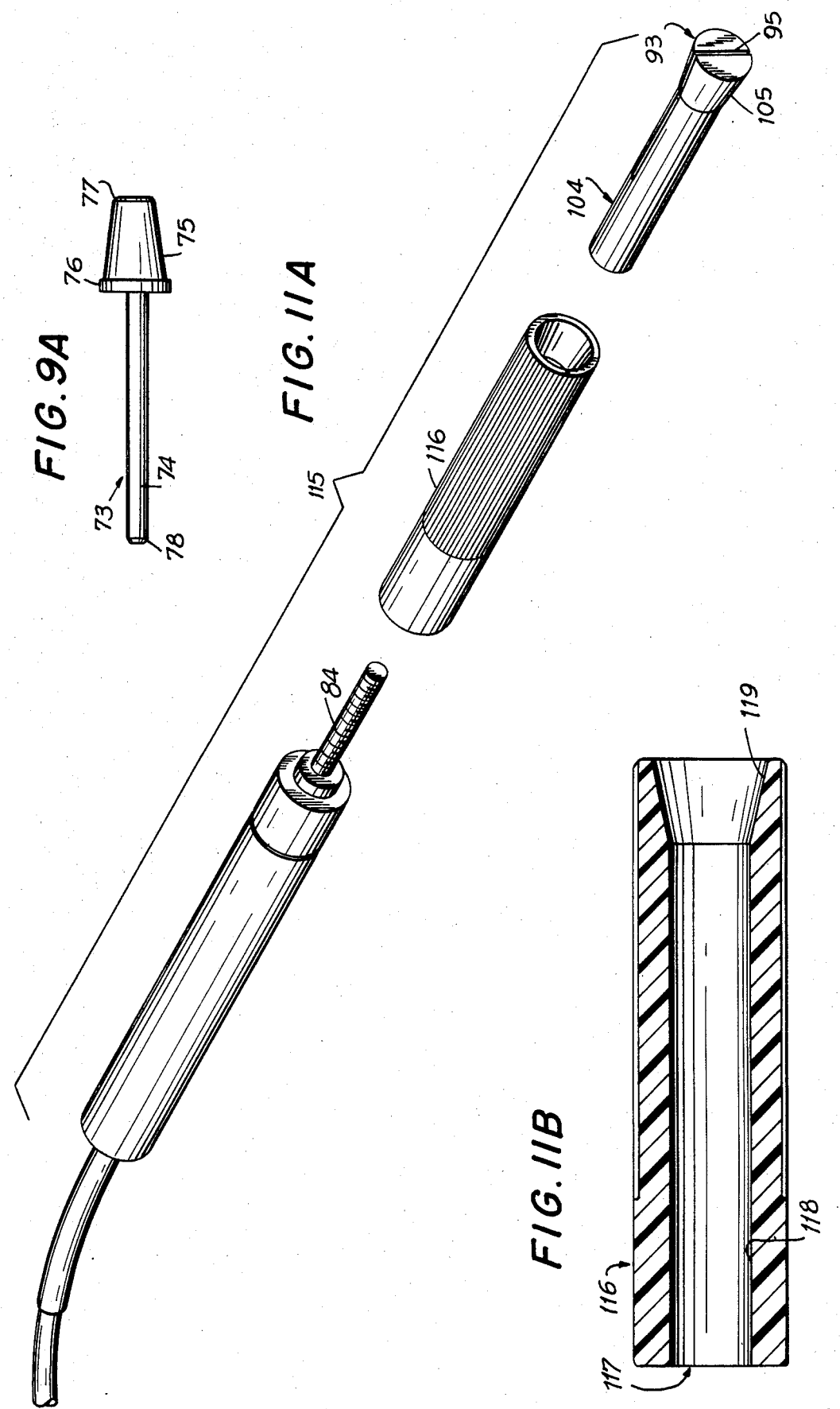

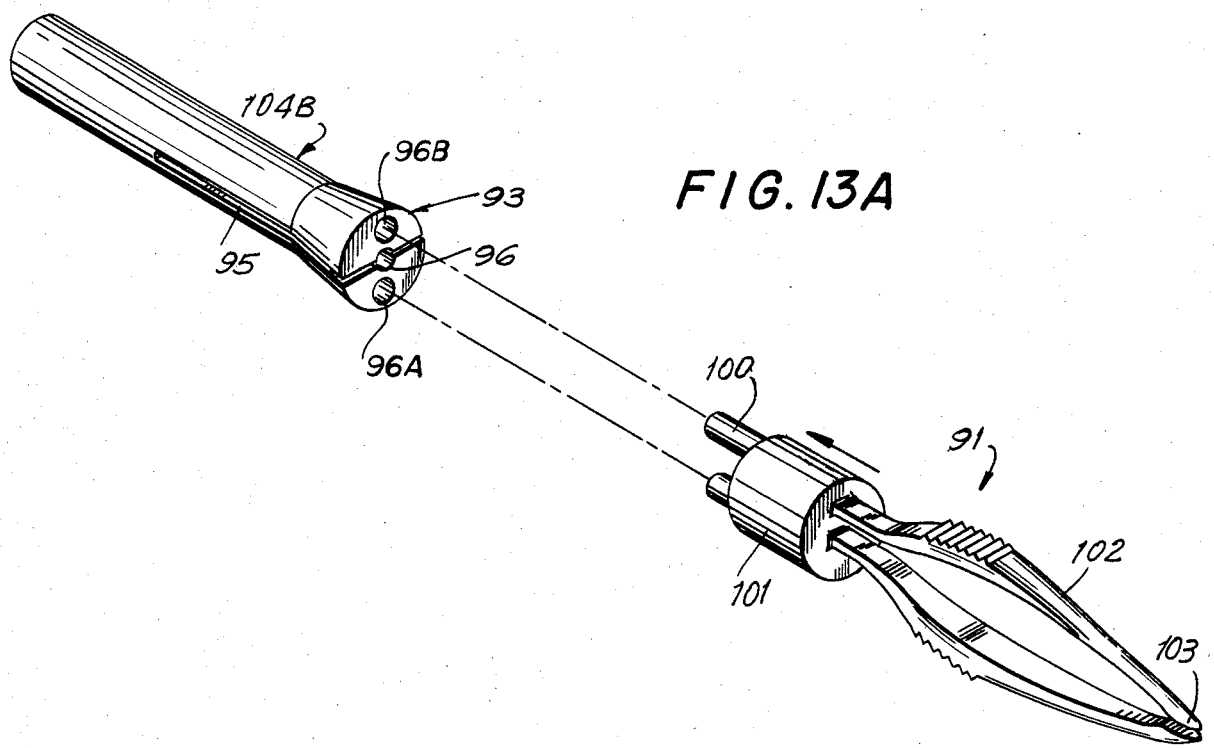
FIG. 13A
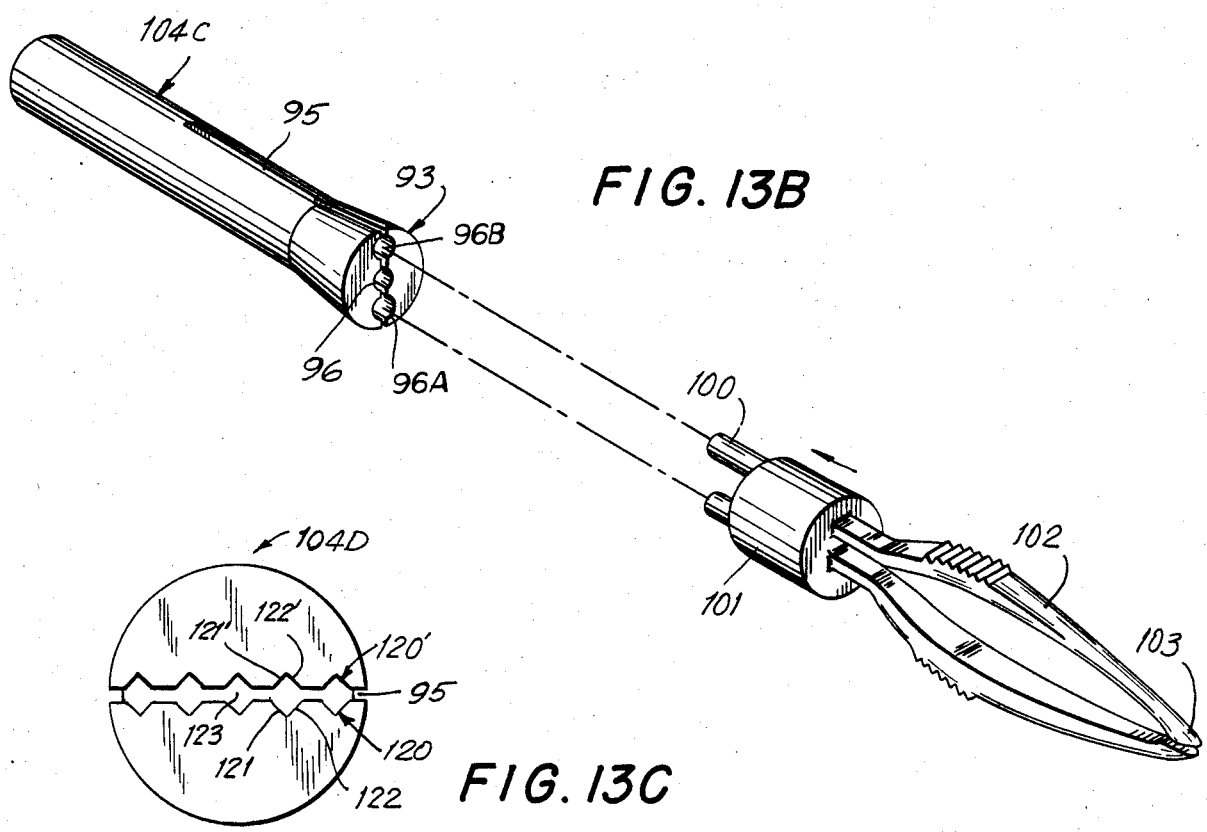
FIG. 13B
FIG. 13C

ELECTROSURGICAL HANDPIECE FOR BLADES, NEEDLES AND FORCEPS

CROSS-REFERENCE TO RELATED APPLICATIONS

This is a continuation-in-part application derived from U.S. patent application Ser. No. 642,521, filed on Aug. 20, 1984.

FIELD OF THE INVENTION

This invention relates to electrosurgery apparatus, and specifically to new handpieces or handpiece adaptors for receiving electrodes in the form of blades, needles and forceps.

BACKGROUND OF THE INVENTION

U.S. Pat. No. 3,730,188, whose contents are hereby incorporated by reference, describes an electrosurgical apparatus for dental use, and in particular describes one form of electrical circuit for generating radio-frequency (RF) currents with different waveform shapes to optimize tissue cutting, hemostasis, or both. A similar apparatus is employed in the medical and veterinarian fields. Different forms of the apparatus are available commercially from a number of suppliers.

In a typical commercial machine, a socket is provided connected to the RF generator on the machine front panel to receive an electrical plug connected at one end of an insulated wire, at the opposite end of which is provided a handpiece to be held by the dentist, veterinarian or physician. The handpiece is configured to receive a removable working electrode by which the RF currents can be applied to the patients' soft tissue for cutting or hemostasis. Typical electrodes commonly in use include needle shapes, wire circular or diamond loop shapes, ball shapes or blade shapes. In addition, a pair of electrodes can be formed as forceps for use in coaptation and pinpoint hemostasis. These electrodes are custom designed for each machine and are thus expensive. In addition, the working end, which usually comprises exposed metal at the tip, is elsewhere enclosed in an insulating layer in order to avoid any RF current leakage to the patient other than from the exposed tip. After use, the electrodes from the handpiece are sterilized for use with the next patient. Aside from the time wasted in the sterilization process, the latter reduces the usable lifetime of the electrode, thus requiring more frequent replacement, adding to the already high cost.

The trend, especially in the medical arts, is toward disposable instruments, which can be discarded after use. There already exist standard-sized disposable scalpel blades and needles which are available at low cost in sterilized packages, for use with non-electrosurgical hand instruments, but these will not fit into the available electrosurgical handpieces.

One supplier of medical electrosurgical equipment has attempted to fill this need by designing new electrosurgical equipment with a new handpiece adapted to receive disposable scalpel blades. But, the equipment is very expensive, and the disposable blades are not of the inexpensive variety, but are custom-designed with internal heating elements regulated by the equipment, the regulated high temperature assumed by the blade during use producing an alleged hemostasis of blood vessels as they are cut. Thus, the need for low-cost equipment with low-cost standard scalpel electrodes is not satisfied by this equipment. Moreover, the handpiece is not capable of receiving various shaped electrodes.

A further disadvantage of the known electrosurgical equipment is that a different handpiece and cord for use with electrocoaptation forceps must be plugged into the RF generating unit. Thus, when a dentist, veterinarian or physician alternatingly uses a scalpel blade or needle and forceps, the respective handpieces and cords must be interchangeably plugged into the unit. This increases the possibility of plugging the handpiece into the wrong jack. In the prior art, it is not possible to use the same handpiece with blades, electrodes, adaptors, and electrocoaptation forceps.

SUMMARY OF THE INVENTION

The principal object of the invention is to provide a novel handpiece that can be employed with existing commercially available electrosurgery equipment and is adapted to receive existing lost-cost commercially available disposable scalpel blades or needles, as well as electrocoaptation forceps. This enables the dentist, veterinarian or physician to switch between, for example, a scalpel blade and forceps without plugging a new cord into the RF generating unit, which is both inconvenient and results in the breaking of sterility, in addition to requiring that the user direct his attention away from the surgical site.

This and other objects and advantages of the invention as will be made clear hereinafter are achieved, in one embodiment, by configuring the handpiece with a collet-type holder or chuck forming an adjustable slot for receiving and holding or clamping a disposable scalpel blade in electrical connection with the RF current-carrying wire of the handpiece. The chuck is adapted in the area of the slot to form a central bore for receiving an electrode, an adaptor for a needle, or an adaptor for electrocoaptation forceps.

In another embodiment, the collet is further provided with a pair of bores on the respective sides of the slot, in which a corresponding pair of pins, attached to the base of the forceps, are inserted, thereby enabling the forceps to be directly mounted into the collet of a standard electrosurgical handpiece.

BRIEF DESCRIPTION OF THE DRAWINGS

The various embodiments of the present invention will now be described with reference to the accompanying drawings, wherein:

FIG. 9A is a side view of the needle adaptor for coupling standard needles to the handpiece;

FIG. 11A is an exploded perspective view of a handpiece in accordance with the invention having a slotted collet for use with scalpel blades;

FIG. 11B is a longitudinal section of the sleeve depicted in FIG. 11A;

FIGS. 13A and B are perspective views of different embodiments of a slotted collet incorporated in the handpiece of the present invention, each capable of receiving scalpel blades, needles, and forceps;

FIG. 13C is an end view of a further embodiment of the handpiece of the present invention.

DETAILED DESCRIPTION OF THE PREFERRED EMBODIMENTS

Figure 1:
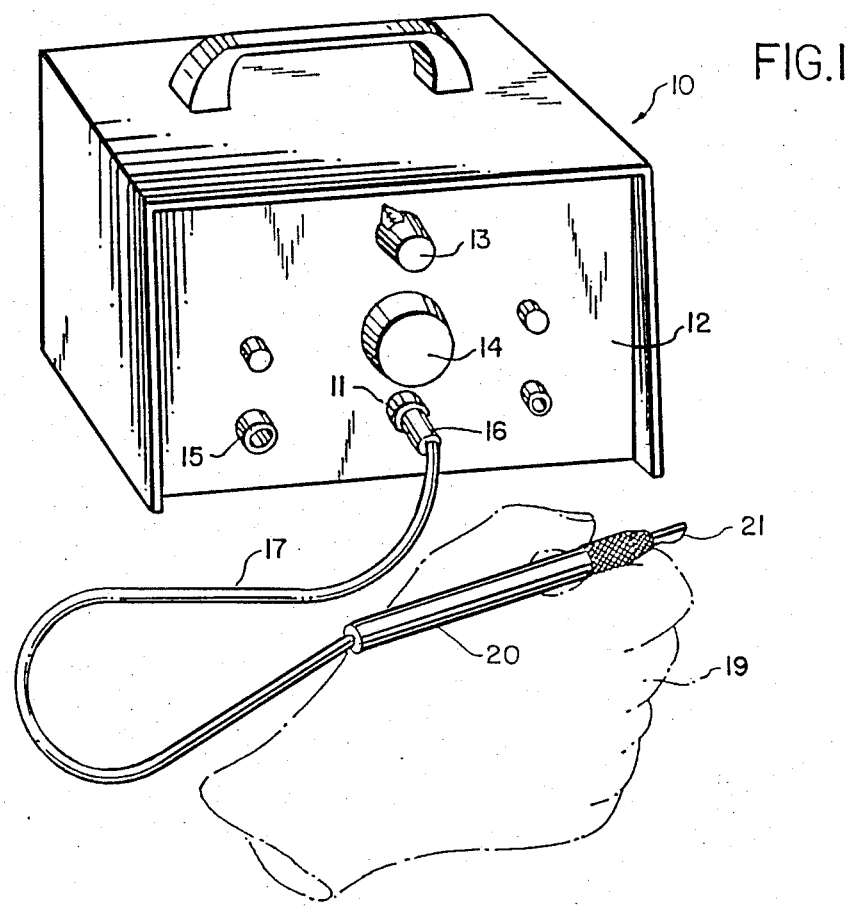
FIG. 1 is a schematic view showing a typical electrosurgical unit to which is connected the handpiece disclosed in co-pending U.S. patent application Ser. No. 642,521.

Referring now to the drawings, FIG. 1 illustrates schematically a conventional form of electrosurgery equipment for dental, medical or veterinarian use, to which has been added one form of the handpiece disclosed in U.S. patent application Ser. No. 642,521. It comprises an apparatus or unit 10 which upon activation manually or by a foot control (not shown) generates RF currents accessible at a socket 11 on the front panel 12. The unit typically includes a switch 13 for controlling the waveforms of the RF currents, as described in the aforementioned U.S. Pat. No. 3,730,188, and a switch 14 for controlling the intensity or amplitude of the currents, which may or may not be regulated. A socket 15 is usually provided for receiving an electrical plug connected to a grounding pad (not shown) which is attached to or held by the patient. Plugged into the RF socket 11 is an electrical plug 16 to which is connected a long electrically insulated cable or wire 17. The cable 17 is in turn permanently connected to one end of a handpiece 20 which at its opposite end contains the working electrode 21, depicted in FIG. 1 as a scalpel blade. The hand of the user (dentist, veterinarian or physician) is shown at 19 holding the handpiece 20 for use on a patient.

Figure 2A:
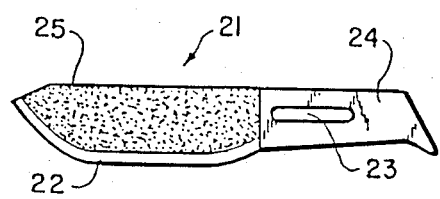
FIGS. 2A, 2B and 2C are side views of typical standard-sized disposable blades.
Figure 2B:
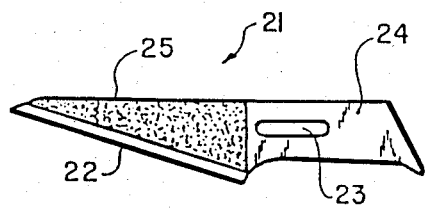
Figure 2C:
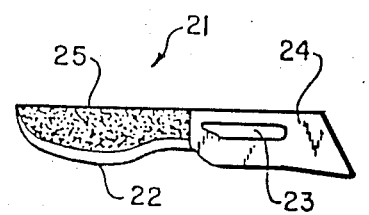

FIGS. 2A, 2B, and 2C illustrate standard forms of disposable scalpel blades which are available commercially in sterilized packages from a number of suppliers. Different shapes of blades defined by standard numbers are available. FIG. 2 illustrates three popular shapes numbered, respectively, Nos. 10, 11 and 15. The blade 21 itself is typically constructed of flat stainless steel with a surgically sharpened edge 22. The rear part 24 of the blade is typically provided with a slot 23 whereby the blade can be removably mounted on a manual handle for use by the physician in a non-electrosurgical procedure. The slot 23 is not used for mounting purposes in the electrosurgical handpiece, of the invention.

The front part of the blade 21 which protrudes from the handpiece is preferably coated, as shown at 25, with an electrically insulating coating that covers all of the exposed blade except for the sharpened edge 22. Teflon is a preferred material for this coating, but other plastics can be substituted. The standard blades are not coated as described, since they are intended for non-electrosurgical applications. The non-coated blades can also be used in the invention, but the addition of the coating 25 is preferred to avoid leakage of RF currents to the patient except at the exposed sharpened edge. The addition of the plastic coating adds only a small extra cost to the manufacture of the blades.

Figure 3:
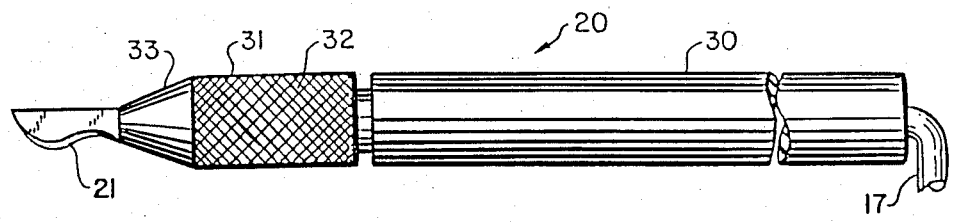
FIG. 3 is an enlarged side view of the handpiece of FIG. 1.

The handpiece 20 with mounted blade 21 is illustrated in FIG. 3. It comprises a straight elongated handle casing 30, constituted of electrically insulating material, for example, of the plastic Baklite or Delrin. The forward portion, in this embodiment, is constituted of a removable cap or sleeve 31, having a knurled surface 32 for easier handling. The front end of sleeve 31 has a tapered surface 33 to avoid blocking of the user's view of electrode 21.

Figure 4:
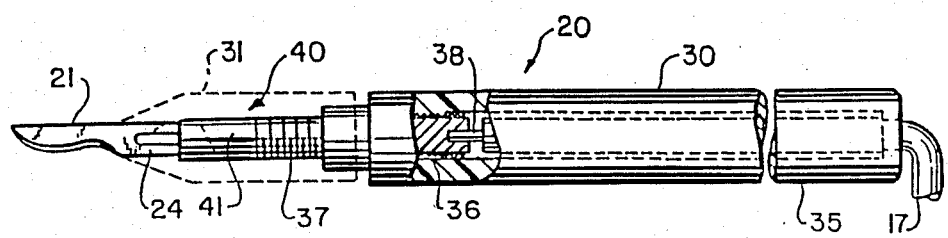
FIG. 4 is a view similar to FIG. 3 but with parts cut away or omitted to show interior details.
Figure 5:
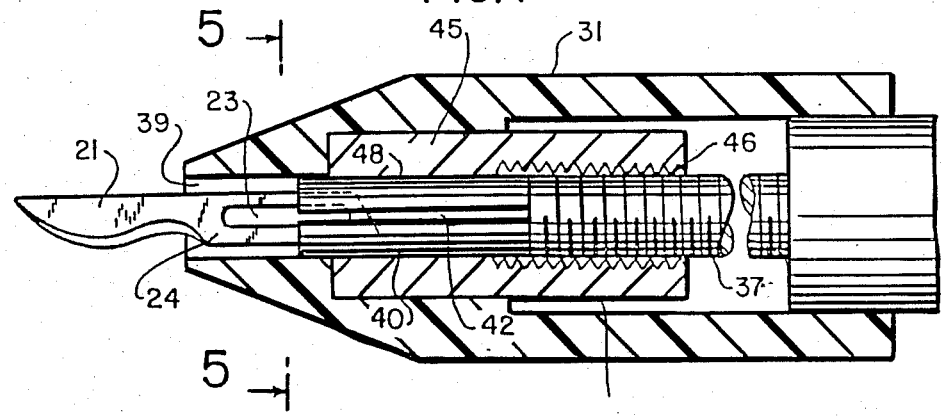
FIG. 5 is a partly cross-sectional view of the front part of the handpiece of FIG. 4 showing further details.
Figure 6:
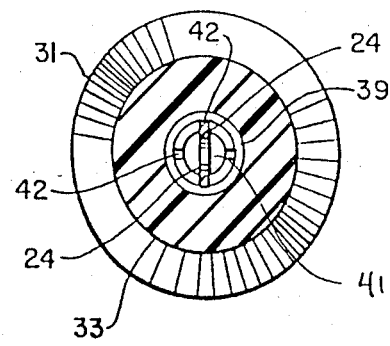
FIG. 6 is a cross-sectional view along the line 5—5 of FIG. 5.

The internal construction of the handpiece 20 is depicted in FIGS. 4–6. The rear portion 35 of the handle is hollow in order to admit the RF cable 17. The cylindrical wall of handle casing 30 forms a bore 36 in which an externally threaded elongated thin bushing or rod 37 is inserted. The bushing is preferably made of brass and at one end has a small bore into which is soldered the internal wire conductor 38 of the cable 17. The rod 37 is of uniform diameter and is threaded over about two-thirds of its length. It is glued in place in the bore 36 of the handle casing. The front end 40 of the rod 37, which is not threaded, functions as a collet or chuck, which is achieved by forming an axial bore 41 along its center, and then providing slits 42 in the side walls thus formed. Four slits are adequate for this purpose, and the slits 42 are preferably provided as two pairs of vertically and horizontally aligned slits, arranged to extend radially at positions separated by 90° (see FIG. 6).

The removable front cap or sleeve 31 has a central bore of varying diameter. The front bore 39 is wide enough to receive the rear or mounting end 24 of the scalpel blade 21. As shown in FIG. 5, the blade rear end 24 is pushed through the bore 39 and into two aligned slits 42 of the collet 40, which slits are wide enough to accommodate the thickness of the flat blade. This action is assisted by making the collet of brass, which renders the slitted end slightly flexible and resilient. On the interior of the cap 31 is mounted a metal insert 45 which has an internal thread 46 adapted to threadingly engage the externally threaded portion of the rod 37, when the cap 31 is placed over the blade and mounted on the handle by rotation clockwise to engage the threads. As the cap 31 advances toward the rear portion 35 of the handle, during this rotation, an internal taper 48 on the insert 45 engages and cams inward on the collet 40, closing the slits 42 and clamping the blade end 24 firmly in the collet 40. When the cap is rotated counterclockwise, the cap 31 retracts and the insert 45 disengages from the collet 40. The slight natural resilience in the collet 40 causes the fingers formed by the slits to return to their unstressed position and the blade end 24 can thus be readily removed by pulling from the collet 40 after use. Note that the slot 23 in the blade mounting portion 24 is not used to mount the blade in the handpiece, yet the blade is held securely in the handpiece.

Figure 7:
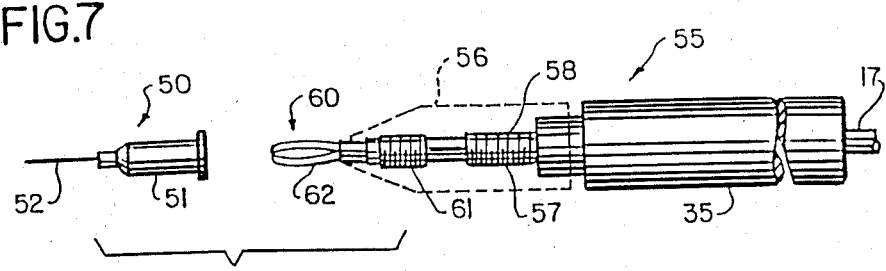
FIG. 7 is a partly exploded view of a second embodiment of the invention disclosed in U.S. patent application Ser. No. 642,521 for use with needles.
Figure 8:
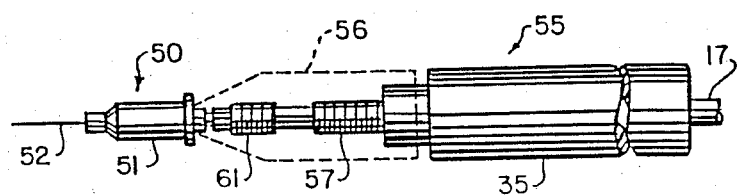
FIG. 8 shows the embodiment of FIG. 7 but with a needle assembled thereon.

The embodiment so far described is used with disposable blades, and cannot in its present form be used to support a disposable needle 50, one standard form of which, also available commercially in various sizes, is depicted in FIGS. 7 and 8. Although the needle diameter and length may vary in the different sizes, the mounting hub is standardized and comprises a slightly flanged hollow hub 51 from which the needle point 52 protrudes. In the second embodiment now to be described with reference to FIGS. 7 and 8, a modified handpiece 55 is employed which is adapted only to support a disposable needle. The same reference numerals are employed as in the first embodiment to designate the same or similar elements. In this second embodiment, the handpiece is designated 55, having the usual handle casing 35 and connecting cable 17. In this case, the front cap 56 is not removable, but is permanently fixed in place, for example, by gluing. A modified bushing or rod 57 is employed, which is anchored as before in the central bore of the handle. The rod 57 is still shown threaded at 58 for better anchoring to the wall, but need not be, since the cap 56 need not be screwed onto it. If desired, however, the cap 56 can be screwed onto it for easier assembly, but need not be removable. The rod 57 extends in the forward direction toward the needle, and on the forward end thereof resilient support 60 for the needle hub 51 is permanently mounted. The support 60, for low cost and simplicity, can be a standard electrical banana-type metal plug, without the usual insulating sleeve, whose wire-receiving end 61 is soldered or welded to the end of rod 57. The plug itself, as shown, comprises a slightly bowed metal band 62 which is resilient and is sized to fit exactly within and firmly support by a friction fit in a detachable manner the needle hub 51. The resilient band 62 of the banana plug as shown protrudes forwardly from the cap 56, and thus the user can easily mount and demount the needle 50 on the resilient plug end. The mounted needle is shown in FIG. 8. Electrical connection is made by way of the cable wire via the metal rod 57 and the banana plug 60 to the metal needle 50 so that when the electrosurgical unit 10 is activated, RF currents can be applied to the patient via the needle point 52.

Figure 9:
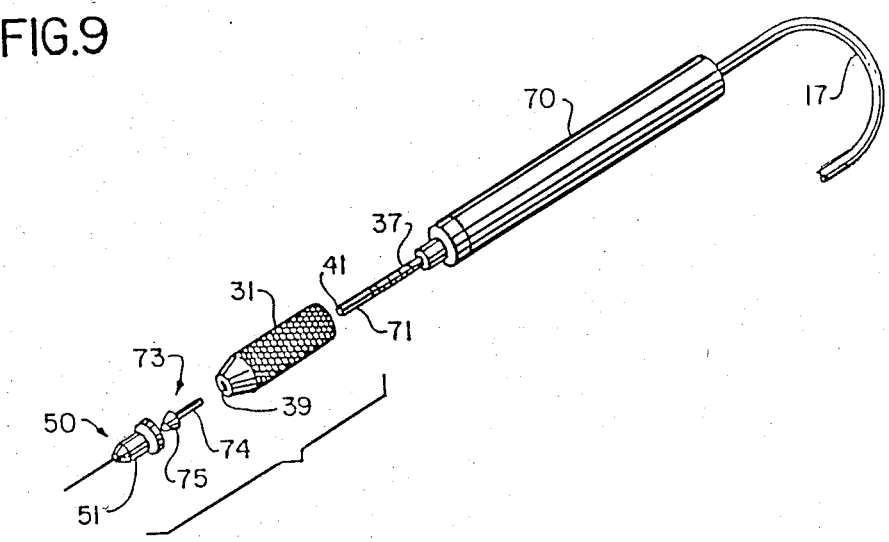
FIG. 9 is an exploded, perspective view of a third embodiment also intended for use with needles.

In the third embodiment depicted in FIG. 9, one form of standard handpiece according to the invention can be used with a novel adaptor for mounting of the disposable needle 50. In this embodiment, the handpiece 70 is provided internally with a collet end 71 similar to the end 40 described in connection with the first embodiment, except the diameter is smaller and the slots are narrower. For example, in this third embodiment, the collet end is preferably about ½ inch long, about 3/32 inch in diameter, having about a 1/16 inch bore and four slits each approximately 1/64 inch wide. In the first embodiment, for the wider scalpel blade, the collet could have the same length, but has a diameter of about 5/16 inch with a bore of about 3/16 inch and with slots about 1/32 inch wide or slightly narrower.

In this third embodiment, the collet bore (see FIG. 6) 41 is adapted to receive and clamp a cylindrical rod about 1/16 or 3/32 inch in diameter. An adaptor or coupling piece 73 is provided, which as shown in FIG. 9, has a cylindrical rod portion 74 of the same diameter as just mentioned, and at its front has a radially widened, contoured head 75 with a diameter chosen to receive in a friction fit the slightly resilient hub 51 of the standard needle 50. To mount the needle 50 to the handpiece, the narrow end 74 of adaptor 73 is inserted in the bore 39 of the removable cap 31, and then into the bore 41 of the slitted end of the collet 71. The cap 31 with metal insert 45 (see FIG. 5), as in the first embodiment, is then rotated clockwise to cam down on the collet 71 to lock the adaptor end 74 into the collet 71. The adaptor head 75 will not pass through the cap bore 39 and thus will protrude from the front of the handpiece. The user then pushes the needle hub 51 onto the protruding adaptor head 75, and the handpiece is ready for use.

A preferred embodiment of the needle adaptor according to the present invention is depicted in detail in FIG. 9A. The pin 74 of adaptor 73 has head 75 integrally formed thereon. Head 75 has a flange 76 which abuts the rim of needle base 51. The top of the head 75 has a 45° C. chamfer 77. The tip of the pin 74 has a similar chamfer 78. The circumferential surface of head 75 has a taper of approximately 3°.

Since what is common to both the first and third embodiments is the internal collect 40, 71 of the handpiece, a handpiece for holding both the scalpel blade and the needle is obtained by using the handpiece construction of the first embodiment and modifying the dimensions of the needle adaptor 73 so that its end 74 can be securely mounted in the bore 41 of collet 71 (see FIG. 6). This modified shape will have a larger-diameter rear portion 74 for the wider bore 41 of collet 40, and a shorter overall length so that when mounted in the collet 40 the enlarged head 75, which has the same dimensions as before, will protrude the same distance from the sleeve 31. The adaptor 73 would be used when the user intends to use the needle electrode. When the scalpel blade is to be used, the adaptor 73 would be removed and the blade end would be inserted directly in the slots 42 of collet 40. Hence, an handpiece capable of receiving both disposable scalpel blades and needles is achieved in this preferred embodiment.

As noted earlier, the scalpel blade can be used with or without the insulating coating 25, although the latter is preferred. The needle can also be provided with an insulating coating. Typical needle sizes are 30 gauge, ½–1 inch long; 27 gauge, ½ inch long; and 23 gauge, 1 inch long. Typical blade dimensions include an overall length of about 1¾ inches, a width or height of about ¼ inch, and a thickness of slightly under 1/64 inch. The handpiece of the third embodiment can be used with or without the RF power at the electrode end.

The major benefit of the third embodiment is to provide an inexpensive, easy-to-manufacture electrosurgical handpiece which is capable of using the packaged, inexpensive, sterile, disposable scalpel blades and needles readily available in the office of every physician, podiatrist or veterinarian, and thus easily available to the dentist. These disposable blades and needles, in comparison with those now available with electrosurgery equipment, are extremely low in cost, typically less than 30 cents each, and thus can be disposed of after use. Furthermore, they are made with great precision and are extremely sharp and anatomically designed and balanced. The blade's wider diameter produces more even, effective coagulation. The needle is typically ridged and is thus strengthened. No complications need be encountered due to the absence of the need for subsequent sterilization. Thus, the handpiece of the third embodiment enables these ubiquitous low-cost blades and needles to be used as electrodes in an electrosurgery procedure, which represents a very valuable contribution to the medical and dental arts by drastically reducing instrument expenses while improving versatility and quality of performance. It is believed that use of such handpieces will improve the professional's ability to carry out all standard electrosurgical procedures.

Figure 10:
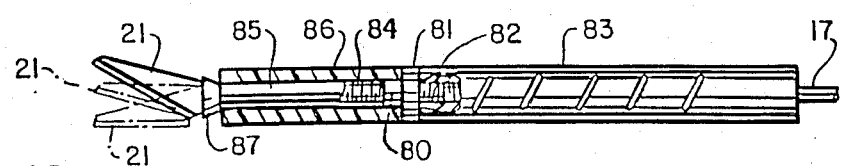
FIG. 10 is an embodiment of the handpiece which was also disclosed in U.S. patent application Ser. No. 642,521.

FIG. 10 shows a variant of the first embodiment, in which the collet can be separated from the support rod. In this case, a metal rod 80 is secured in a central insulating collar 81. The rod 80 can be screwed into the hollow handle casing 83 by means of threads 82. Handle casing 83 functions similarly to the wall 36 in FIG. 4. The cable 17 is connected to the end of collet 85, which is sandwiched between an insulating cylindrical sleeve 86 and the threaded support rod 84. The end 87 of collet 85 is radially widened and coacts with the cylindrical sleeve 86 to cam down and clamp the collet when the collet is rotated clockwise on the threaded support rod 84. The collet end depicted in FIG. 10 has only one slit for receiving the scalpel blade, which slit is narrowed as the sleeve 86 cams down on the collet 85. In a further embodiment, the collet may be provided with a central bore at its slitted end for receiving an electrode or an adaptor, as depicted in FIG. 5. However, it should be noted that the collet depicted in FIG. 10 projects slightly forwardly of the sleeve 86. The device functions similarly to that depicted in FIG. 5 except that the forward protrusion of the collet end 87 allow the scalpel blade to be angled upward or downward in the vertical plane up to about 30° and clamped in that position. This allows the user to locate the blade 21 in a position more suitable for a particular procedure. Also, if desired, ribs, cradles or grooves can be provided along the surface of the handle to increase the user's tactile sense and control.

Although the third embodiment depicted in FIG. 9 (and FIG. 6) provides the advantage that blades, electrodes, and needles can be interchangeably used with a single handpiece, the preferred embodiment of the present invention provides the further advantage that electrocoaptation forceps can also be interchangeably used with the same handpiece. This can be achieved by providing a novel adaptor for use with the handpiece depicted in FIGS. 6, 9, 10, and 12A, or by providing a novel handpiece in which the collet has a slit, a central axial bore, and a pair of diametrically opposite axial bores arranged on opposing sides of the slit for interchangeably receiving respectively a scalpel blade, an electrode or adaptor, or the pins of forceps.

FIG. 11A is an exploded perspective view of an embodiment of the handpiece in which the collet 104 has a slit 95 for receiving a scalpel blade. Collet 104 comprises a cylindrical portion having a threaded bore (not shown) for engaging threaded support rod 84. The collet is inserted in insulating cylindrical sleeve 116, which has a bore 117 comprising a cylindrical bore 118 and a tapered bore surface 119 of increasing diameter, before being threadingly coupled to support rod 84. The collet 104 further comprises a section having a circumferential conical surface 105, the diameter of which increases in the direction of end face 93. Furthermore, the bore surface 119 of increasing diameter, e.g. a conical bore surface, engages and cams down on conical surface 105 when collet 104 is fully screwed onto support rod 84. As a result of this camming effect, pressure is applied on conical surface 105 of collet 104, which causes the respective portions of collet 104 on either side of slit 95 to flex resiliently, whereby the width of slit 95 at end face 93 is reduced. These compressive forces applied to conical surface 105 enable the slit 95 to securely grip the mounting portion of a scalpel blade inserted therein.

Figure 12A:
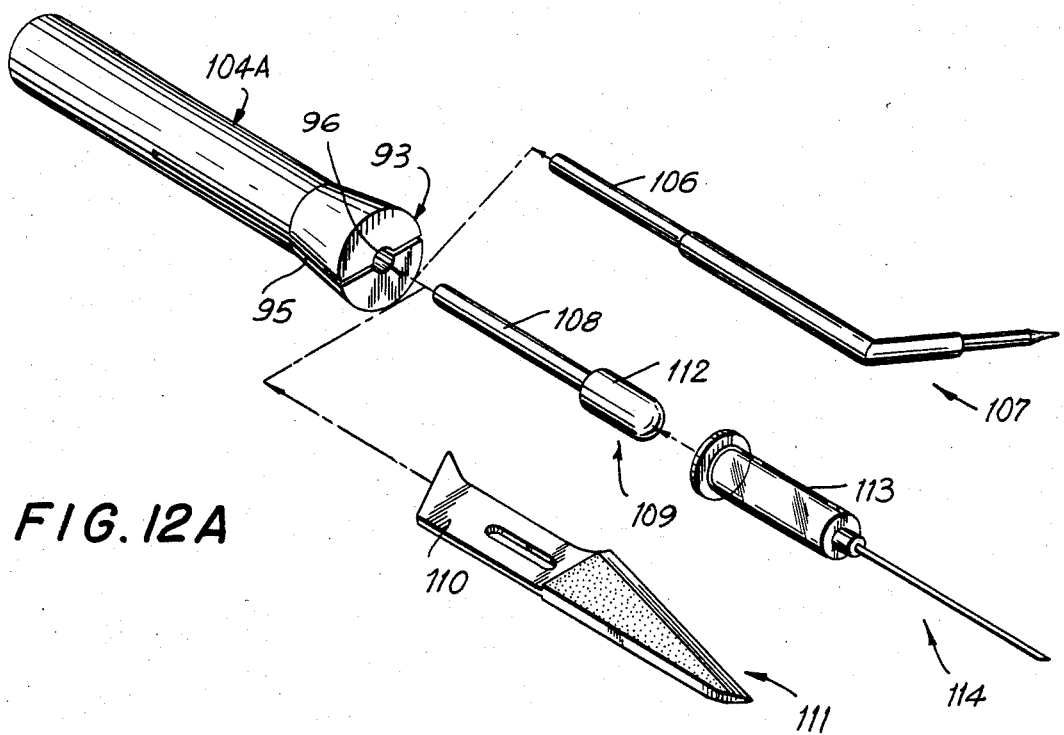
FIG. 12A is a perspective view of a slotted collet according to the invention for use with scalpel blades, having a central bore for receiving the pins of various electrodes or a needle adaptor.

FIG. 12A shows a second embodiment of the collet incorporated in the handpiece of FIG. 11A. In this embodiment, in addition to slit 95, the collet 104A is provided with a central axial bore 96 for receiving the pin of an adaptor or electrode. For example, the central bore 96 is adapted to receive pin 106 of electrode 107 and pin 108 of needle adaptor 109. The slit 95 is adapted to receive the end portion 110 of scalpel blade 111. The head of needle adaptor 109 is in turn adapted for insertion in the base 113 of needle 114. It should be noted that the collet in FIG. 12A (and FIGS. 12B and 13) is depicted in an enlarged scale relative to the depicted elements to be coupled therewith.

In this embodiment, as a result of the camming effect produced as the sleeve bore engages the conical surface 105 of collet 104A during screwing of collet 104A onto support 84 (see FIG. 11A), the width of slit 95 decreases. Furthermore, as should be apparent, as the width of slit 95 decreases, the distance between the opposing surfaces of central bore 96 decreases. Thus, the camming effect of sleeve 116 on collet 104A will cause the bore 96 to exert radially inwardly directed forces on a pin inserted therein.

Figure 12B:
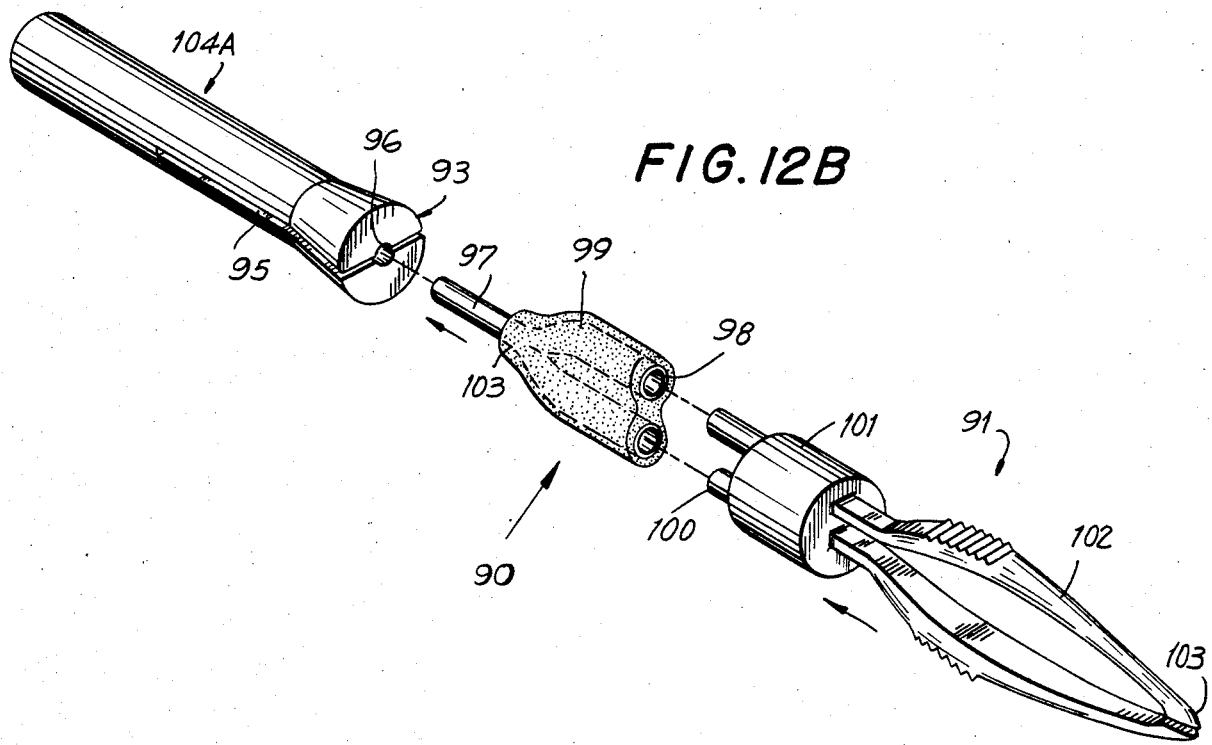
FIG. 12B is a perspective view of the slotted collet with central bore of FIG. 12A, showing forceps and the forceps adaptor which can be used to couple the forceps to the handpiece.

FIG. 12B shows the preferred embodiment of an adaptor 90 for coupling the electrocoaptation forceps 91 to handpiece 115. The collet 104A of this handpiece is identical to that depicted in FIG. 12A.

As previously described, slit 95 is formed to receive a scalpel blade and central bore 96 is formed to receive the pin of an adaptor or an electrode. In particular, central bore 96 is able to receive metal pin 97 of the forceps adaptor 90. When the sleeve of handpiece 115 is cammed down on the end of collet 104A during rotation, as previously described, the central bore 96 narrows and engages pin 97, whereby adaptor 90 is held securely in the handpiece.

At the other end of the adaptor 90, two bores 98 are provided for receiving the pins 100 of forceps 91. In particular, bores 98 may be formed by a pair of metal tubes (denoted by dashed lines) embedded in elastic insulating body 99. The tubes 98 are both electrically and physically connected to pin 97 by means of junction 103 (denoted by dashed lines), thereby forming a wishbone-type construction. The walls of the tubes are sufficiently thin to enable resilient flexure of the tubes in a lateral direction. The adaptor 90 conducts the RF current from handpiece 115 to forceps 91. Insulating body 99 protects the patient against RF current leakage. The wishbone construction is preferably made of brass. Because insulating body 99 is made of resilient material, the embedded tubes forming bores 98 are still able to flex.

Forceps 91 comprises a cylindrical base 101 having a pair of pins 100 integrally formed at one end and a pair of pincers 102 integrally formed at the other end. The base is comprised of insulating material, while the surface of the pincers is coated with an insulating material such as Teflon, except at the tips 103 of pincers 102. The pincers 102 and pins 100 are connected by suitable conductors (not shown) embedded in base 101. The pins 100 are rigidly affixed to the base 101, whereas pincers 102 are adapted to flex in the plane of the pincers, as a result of which the tips 103 of pincers can be pressed into contact with each other. The pincer tips 103 are applied to bleeding tissue at the point of the incision for performing pinpoint hemostasis. The RF current generated produces a spark between the tips that seals off the bleeding vessel and stops the bleeding.

The tubes forming bores 98 in adaptor 90 are deliberately separated by a distance slightly different than the distance separating rigid pins 100 of forceps 91. As a result, the tubes must be flexibly displaced to enable bores 98 to accommodate pins 100. This flexure produces a restorative force in the tubes which acts on the pins 100 to hold them securely in position during coupling of the adaptor and forceps.

Thus, the adaptor 90 of the present invention enables standard forceps to be coupled to a standard electrosurgical handpiece.

In a further embodiment of the present invention, the handpiece is provided with a collet 104B as depicted in FIG. 13A. The collet 104B differs from the collet depicted in FIGS. 12A and 12B in that a pair of additional axial bores 96A and 96B are formed to extend from the endface 93 of the collet 104B, on either side of the gap formed by central bore 96 and slit 95. These bores 105 are adapted to receive the pins 100 of forceps 91.

It should be noted that the outer surface of collet 104B is configured, as are collets 104 (FIG. 11A) and 104A (FIG. 12A), to engage the tapered bore surface 119 of sleeve 116 as the collet is screwed onto threaded support rod 84. During rotation and corresponding displacement of collet 104B, the tapered bore surface 119 cams down on the collet, whereby the gap formed by slit 95 and central bore 96 is narrowed. This enables the collet to securely hold the pin of an electrode or adaptor or the end of a scalpel blade. Furthermore, as should be apparent, as the width of the gap decreases, the distance separating the bores 105 decreases. Thus, if pins 100 are inserted in bores 96A and 96B, the camming effect produced by the tapered bore surface 119 during screwing on of the collet will cause bores 96A and 96B to exert radially inwardly directed forces on pins 100, with the frictional forces thereby generated securely coupling the forceps 91 to handpiece 115.

In another embodiment of the invention, the handpiece is provided with a collet 104C as depicted in FIG. 13B. The collet 104C differs from the collet 104B depicted in FIG. 13A in that the pair of diametrically opposed axial bores 96A and 96B are located along the slit 95. Thus, the central axial bore 96 and the axial bores 97A are formed by respective opposing grooves formed in the opposing surfaces which define slit 95.

The outer surface of collet 104C is again configured to engage the tapered bore surface 119 of sleeve 116 as the collet is screwed onto threaded support rod 84. During rotation and corresponding displacement of collet 104C, the tapered bore surface 119 cams down on the collet, whereby the gap formed by slit 95, central bore 96, and offset bores 96A and 96B is narrowed. As previously described, compressive forces are applied on the element inserted in the gap as a result of this narrowing, whereby the element is held securely in place. In the case of the coaptation forceps, the pins 100 are respectively inserted in bores 97A and securely held in place by the compressive forces exerted transverse to the plane of slit 95.

Figure 14:
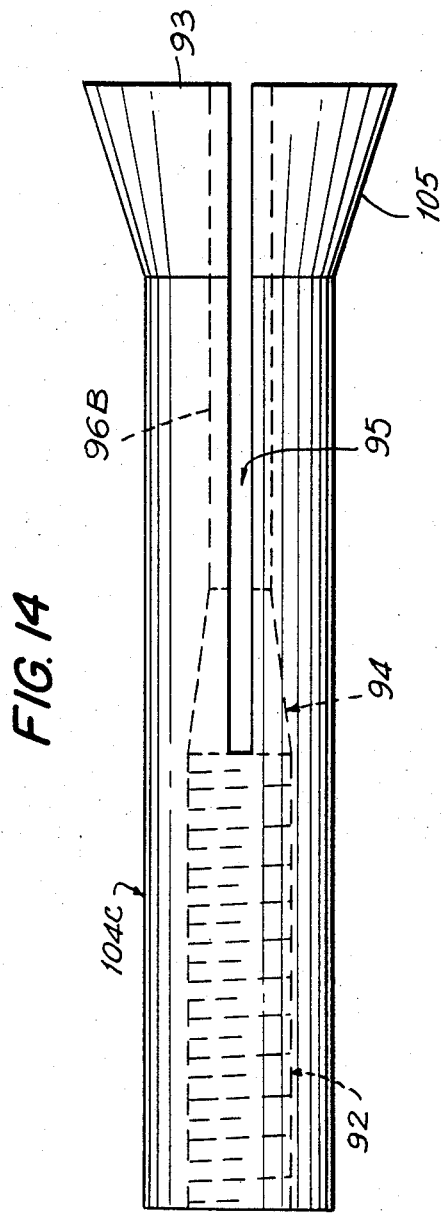
FIG. 14 is a side view of the collet shown in FIG. 13B.

FIG. 14 is a side view of the collet 104C shown in FIG. 13B, showing the threaded bore 92 for engaging threaded support rod 84 (shown in FIG. 11A) and one of the diametrally opposed bores 96B, both of bores 92 and 96B being indicated by dashed lines. The bores 92 and 96B communicate by way of a conical bore 94 in the embodiment shown in FIG. 14, although this is not necessary.

Thus, the embodiments depicted in FIGS. 12B, 13A, and 13B enable the same electrosurgical handpiece to be used with interchangeable accessories, including scalpel blades, needles, electrodes and forceps.

Finally, in another embodiment of the invention, instead of the axial grooves of semicircular cross section formed in the opposing internal surfaces which define the slit, axial grooves of triangular cross section can be provided as depicted in the end view of FIG. 13C. The collet 104D of FIG. 13C again has a slit 95 defined by confronting internal surfaces. First and second pluralities of parallel axial grooves 120 and 120' of triangular cross section were arranged in opposing relationship in the respective internal surfaces. Each groove 120 is defined by planar surfaces 121 and 122 which lie parallel to the collet axis 123 and which join at the apex of the triangular or V-shaped groove. Each pair of opposing grooves 120 and 120' is arranged to engage a pin of round cross section and hold the pin therebetween during radial compression of the collet as previously described.

The preferred embodiment of FIG. 13C has the following advantages. First, a pin can be inserted in and firmly held by any one of the opposing pairs of triangular grooves, allowing adjustment of the position of the pin as needed. Second, the opposing triangular grooves can receive pins of different diameter. In contrast, in the embodiment depicted in FIG. 13B, the grooves of semicircular cross section are adapted to receive a pin of predetermined diameter. A pin of smaller diameter would not be optimally secured in the lateral direction (i.e., along the plane of the slit) in a groove of semicircular cross section, whereas in the embodiment of FIG. 13C, the respective surfaces 121, 122 and 121', 122' engage the circular pin at four separate points, thereby preventing even slight lateral movement of the pin. The embodiment depicted in FIG. 13C is shown with five bores, although it may have only two bores, formed in the above-described manner, for receiving two pins of electro-coaptation forceps or one pin of an electrode or adaptor. Alternatively, an embodiment can be formed to have only one bore of triangular cross section for receiving the pin of a needle adaptor, a forceps adaptor, or an electrode.

The foregoing description of the preferred embodiment is presented for illustrative purposes only and is not intended to limit the scope of the invention as defined in the appended claims. Modifications may be readily effected by one having ordinary skill in the art without departing from the spirit and scope of the inventive concept herein disclosed. In particular, the handpiece of the present invention can be electrically connected to the mounted electrode by means of a switch arranged on the handpiece, as taught in U.S. Pat. No. 4,463,759.

What is claimed is:

1. A handpiece for use with a current-generating unit and adapted to receive a plurality of different electrosurgical electrodes, comprising:
  (a) an elongated handle casing made of insulating material and having an axis;
  (b) a terminal located inside said handle casing;
  (c) an insulated lead extending from said handle casing and electrically connected to said terminal;
  (d) an elongated collet made of metal and having an axis, said collet being electrically connected to said terminal and mechanically coupled to said handle casing such that said collet axis is substantially parallel to said handle casing, and said collet having a central bore formed along a portion of said collet axis and extending from an endface, a slit extending along a plane through said collet axis, and a pair of axial bores extending from said endface and diametrically arranged with respect to said central bore; and (e) a sleeve made of insulating material and having a bore adapted to receive said collet, wherein the surface at one end of the bore of said sleeve has an inner diameter less than the outer diameter of said collet at said endface, said surface of said one end of the bore engaging an outer circumferential surface of said collet in the vicinity of said endface at a first axial position of said collet relative to said handle casing.

2. The handpiece as defined in claim 1, wherein said diametrically arranged axial bores are arranged on opposite sides of the gap formed by said slit and said central bore.

3. The handpiece as defined in claim 1, wherein said diametrically arranged axial bores are arranged along said slit.

4. The handpiece as defined in claim 1, further comprising a metal threaded member electrically connected to said terminal and rigidly supported by said handle casing, wherein said collet has a threaded bore for rotatably engaging said threaded member.

5. The handpiece as defined in claim 1, wherein the bore surface of said sleeve is substantially cylindrical and the outer surface of said collet in the area of said endface is radially outwardly tapered, said surfaces being arranged such that the bore surface of said sleeve abuts said tapered surface in the assembled state.

6. The handpiece as defined in claim 1, wherein the bore surface of said sleeve has a radially inwardly tapered portion and the outer surface of said collet is substantially cylindrical, said surfaces being arranged such that the tapered surface of said sleeve abuts the outer surface of said collet in the area of said endface in the assembled state.

7. A handpiece for use with a current-generating unit and adapted to receive a plurality of different electrosurgical electrodes, comprising:

(a) an elongated handle casing made of insulating material and having an axis;

(b) a terminal located inside said handle casing;

(c) an insulated lead extending from said handle casing and electrically connected to said terminal;

(d) an elongated collet made of metal and having an axis, an outer surface, and an end face substantially transverse to said collet axis, said collet being electrically connected to said terminal and mechanically coupled to said handle casing such that said collet axis is substantially parallel to said handle casing, and said collet having a planar slit which intersects a portion of said collet axis and extends from said end face, said slit forming a pair of opposing internal surfaces, each of said internal surfaces having first and second axial grooves formed therein, said first grooves being in opposing relationship and said second grooves being in opposing relationship, and (e) a sleeve made of insulating material and having a bore adapted to receive said collet;

wherein the surface at one end of the bore of said sleeve has an inner diameter less than the outer diameter of said collet at said endface, said surface of said one end of the bore engaging an outer circumferential surface of said collet in the vicinity of said endface at a first axial position of said collet relative to said handle casing.

8. The handpiece as defined in claim 7, wherein each of said grooves has a triangular cross section.

9. The handpiece as defined in claim 7, wherein each of said grooves has a substantially semicircular cross section.

10. A handpiece for use with a current-generating unit and adapted to receive a plurality of different electrosurgical electrodes, comprising:

(a) a substantially cylindrical handle casing made of insulating material, said handle casing having first and second end faces, each of said end faces having an opening formed therein;

(b) a terminal arranged inside said handle casing;

(c) an insulated lead electrically connected to said terminal and extending through the opening formed in said first end face of said handle casing;

(d) a metal threaded member electrically connected to said terminal and extending through the opening formed in said second end face of said handle casing, said threaded member being rigidly supported by said handle casing;

(e) a metal collet rotatably mounted on said threaded member and having a cylindrical portion defining an axis and a radially outwardly tapered portion, said cylindrical portion having a threaded surface for threadingly engaging said threaded member, and said radially outwardly tapered portion having a central bore formed therein extending along a portion of said collet axis, a slit extending along a plane through said collet axis, and a pair of axial bores diametrically arranged with respect to said central bore; and (f) a sleeve made of insulating material having a bore adapted to receive said collet, wherein the surface at one end of the bore of said sleeve has a diameter less than the maximum diameter of said tapered portion, said surface of said one end of the sleeve bore engaging said radially outwardly tapered portion of said collet at a first axial position of said collet relative to said threaded member, said tapered portion undergoing increasing compression in response to further rotation of said collet in a first direction relative to said threaded member.

11. The handpiece as defined in claim 10, wherein said slit has an axial length sufficient to enable the portions of said collet formed by said slit to flex such that the respective endfaces of said collet portions are deflected radially inwardly by an amount substantially equal to the difference between said outer diameter of said collet in the vicinity of said end faces and said inner diameter of said sleeve bore at said one end during compression of said tapered portion of said collet.

12. The handpiece as defined in claim 10, wherein said collet is made of brass.

13. The handpiece as defined in claim 10, wherein said threaded member comprises a pin and said threaded surface of said collet comprises a bore.

* * * * *